United States Patent [19]

Muntwyler et al.

[11] 4,219,593
[45] Aug. 26, 1980

[54] METHOD OF PROTECTING KERATINOUS MATERIAL FROM ATTACK BY INSECTS THAT FEED ON KERATIN

[75] Inventors: René Muntwyler, Hofstetten; Bernardo de Sousa, Basel, both of Switzerland

[73] Assignee: Ciba-Geigy Corporation, Ardsley, N.Y.

[21] Appl. No.: 51,555

[22] Filed: Jun. 25, 1979

[30] Foreign Application Priority Data

Jul. 6, 1978 [CH] Switzerland ............ 7381/78

[51] Int. Cl.² .............................. B22B 9/02
[52] U.S. Cl. .................. 428/15; 106/15.05; 106/18.35; 427/384; 427/421; 427/428; 428/270; 428/473; 428/907
[58] Field of Search ........ 427/384, 421, 428; 106/15.05, 18.35; 428/270, 907, 15, 473

[56] References Cited

U.S. PATENT DOCUMENTS

| | | | |
|---|---|---|---|
| 1,955,891 | 4/1934 | Salzberg et al. | 428/907 |
| 2,134,001 | 10/1938 | Mills et al. | 428/907 X |
| 2,362,768 | 11/1944 | Morgan et al. | 428/907 X |
| 3,968,298 | 8/1972 | Reinert et al. | 428/270 |

FOREIGN PATENT DOCUMENTS

1444067 10/1968 Fed. Rep. of Germany ........ 428/907

*Primary Examiner*—Shrive P. Beck
*Attorney, Agent, or Firm*—Prabodh I. Almaula

[57] ABSTRACT

A method of protecting keratinous material from attack by insects that feed on keratin and from feeding damage, which comprises treating the material to be protected with compounds of the formula

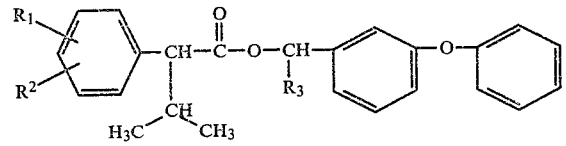

wherein each of $R_1$ and $R_2$ independently represents hydrogen, fluorine, chlorine, bromine, alkyl of 1 to 4 carbon atoms or alkoxy of 1 to 4 carbon atoms, or $R_1$ and $R_2$ in the ortho-position to each other together represent the methylenedioxy radical, and $R_3$ represents hydrogen, cyano, —C≡CH of —CH=CH₂.

17 Claims, No Drawings

METHOD OF PROTECTING KERATINOUS MATERIAL FROM ATTACK BY INSECTS THAT FEED ON KERATIN

The present invention relates to a method of protecting keratinous material, especially wool, woollen goods, hides, furs and feathers, from attack by insects that feed on keratin and from feed damage, in particular from attack by moths and other pests that feed on keratin, which comprises treating said keratinous substrates with specific esters of phenylisopropylacetic acid.

It is known from the literature that various natural pyrethrins and many synthetic pyrethroids have been investigated for their suitability as mothproofers. However, on account of their relative instability to light and air, these compounds generally afford a very short-term protection. One synthetic pyrethroid, 3-phenoxybenzyl 2,2-dimethyl-3-(2,2-dichlorovinyl)cyclopropane carboxylate, has been described as a useful mothproofer (see J. Text. Inst. 1976, Vol. 67 No. 3, 77–81, Man. Chem. & Aerosol News, October 1977, 39–40, and Japanese patent specification No. 1,133,600). It is also known from German Offenlegungsschrift Nos. 2,335,347 and 2,365,555 that different substituted acetates are active insecticides, especially crop insecticides.

The present invention is based on the surprising observation that a specific group of phenoxybenzyl esters of α-phenyl-α-isopropylacetic acid, namely those of the formula

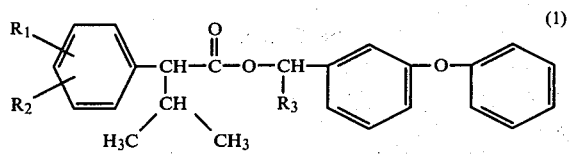

wherein each of $R_1$ and $R_2$ independently represents hydrogen, fluorine, chlorine, bromine, alkyl of 1 to 4 carbon atoms or alkoxy of 1 to 4 carbon atoms, or $R_1$ and $R_2$ in the ortho-position to each other together represent the methylenedioxy radical, and $R_3$ represent hydrogen, cyano, —C≡CH or —CH=CH$_2$ are particularly outstanding protectants against insects that feed on keratin, for example moths.

Accordingly, the present invention provides a method of protecting keratinous material from attack by insects that feed on keratin and from feeding damage caused by such insects, which comprises treating the material to be protected with compounds of the formula (1). The invention also relates to the use of compounds of the formula (1) as protectants for keratinous material against insects that feed on keratin and to the material proofed with compounds of the formula (1).

Preferred compounds of the formula (1) for use in the method of the present invention are those of the formula

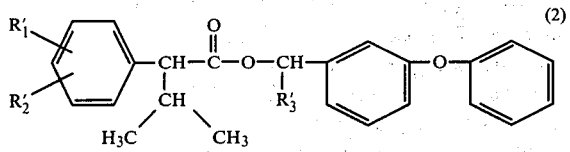

wherein each of $R'_1$ and $R'_2$ independently represents chlorine, bromine, methyl or methoxy, or $R'_1$ and $R'_2$ in the 3,4-position together represent the methylenedioxy radical, and $R'_3$ represents hydrogen, cyano or —C≡CH.

Particularly good results are obtained with those compounds of the formula (1), wherein $R_1$ represents hydrogen, fluorine, chlorine, bromine, alkyl of 1 to 4 carbon atoms or alkoxy of 1 to 4 carbon atoms, and $R_2$ represents hydrogen, and most particularly with those compounds of the formula (1), wherein $R_1$ represents fluorine, chlorine, bromine, methyl or methoxy, $R_2$ represents hydrogen and $R_3$ represents cyano or —C≡CH, and also with compounds of the formula (1), wherein $R_1$ and $R_2$ represent hydrogen and $R_3$ represents hydrogen or —CH=CH.

The most preferred compounds for use in the method of the present invention are those of the formulae

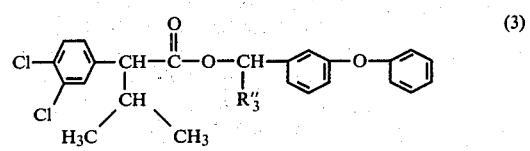

and

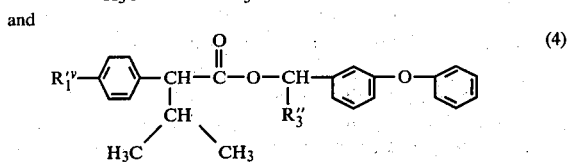

wherein $R'^{\nu}_1$ represents chlorine or methyl and $R''_3$ represents cyano or —CH=CH.

The compounds of the formula (1) used in the method of the invention possess an excellent action against insects that feed on keratin, for example against Lepidoptera larvae, such as Tineola spec. and Tinea spec., and against Coleoptera larvae, for example Anthrenus spec. and Attagenus spec. The active substances of the formula (1) are preeminently suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool, products made of other animal hairs, hides, furs and feathers.

A particularly important feature of the compounds of the formula (1) used in the method of the invention is their action against the larvae of the webbing clothes moth (Tineola bisselliella) and common clothes moth (Tinea pellionella) as well as against the larvae of the fur beetle and carpet beetle (Attagenus spec. and Anthrenus spec. respectively). The method of the present invention is therefore preferably used on the one hand for protecting woollen textiles, for example blankets, wool carpets, woollen underwear, woollen clothing and knits, and also blends, one component of which is wool, for example blends of wool and other natural fibres, preferably cotton, or of wool and synthetic fibres, and, on the other hand, also for protecting furs and skins from attack by the above-mentioned pests.

The compounds of the formula (1) are applied to the above substrates, in particular to woollen textiles and wool blends, preferably by methods commonly known and employed in dyeing, such as the exhaust method and padding. To this end, an aqueous dispersion (emulsion or suspension) of the respective active substance is prepared. The active substance is preferably dissolved beforehand in an organic solvent, such as an aliphatic or alicyclic alcohol, a ketone, a hydrocarbon, such as benzene, a xylene, toluene, petroleum distillate, and also a chlorinated or fluorinated hydrocarbon, especially in propylene glycol, methoxy ethanol, ethoxy ethanol or dimethyl formamide, and then added to the treatment bath, which can contain additional assistants conventionally used in dyeing, for example dispersants. The organic stock formulation can already contain such assistants.

The aqueous dispersions contain, for example, surfactants, for example anionic compounds, such as soaps and other carboxylates (e.g. alkali metal salts of higher fatty acids), derivatives of sulfur oxyacids (e.g. the sodium salt of dodecylbenzenesulfonic acid, water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher molecular acetylene glycols, polyglycol ethers (e.g. polyglycol ethers of higher fatty alcohols, polyglycol ethers of higher molecular alkylated phenols). The liquor can additionally contain further conventional assistants, such as water-soluble perborates, polyphosphates, carbonates, silicates, fluorescent whitening agents, plasticisers, carbonates, salts with acid reaction, such as ammonium or zinc silicofluoride, or certain organic acids, such as oxalic acid, acetic acid or, in particular, formic acid, and also antimicrobial agents and finishing agents, for example those based on synthetic resins or starch.

The textile material can be impregnated, for example, with the active substances by means of dye, bleaching, chroming or aftertreatment baths, whilst various textile finishing methods are possible, for example the pad or exhaust method.

The treatment is carried out advantageously at temperatures from 10° to 100° C., for example at 10° to 70° C., but preferably at about room temperature.

Because of their good solubility in organic solvents, the active compounds of the formula (1) can also be very easily applied from non-aqueous media to the substrates to be protected (solvent application). Suitable solvents in this connection are, inter alia, trichloroethylene, methylene chloride, hydrocarbons, propylene glycol, methoxy ethanol, ethoxy ethanol, dimethyl formamide, to which dispersing agents (e.g. emulsifiers, such as sulfated castor oil, fatty alcohol sulfates etc.) and/or other assistants can be added. The material to be protected is usually simply impregnated with these solutions.

The proofing of the material to be protected can also be combined with a dry cleaning process. To this end, the active compounds are dissolved in the cleansing agent (such as a lower halogenated alkane, for example trichloroethylene etc.) and the cleaning process is carried out in the usual manner.

However, the active compounds can also be dissolved in readily volatile organic solvents and the resulting solution then sprayed onto the substate (spray application). Textile fabrics, furs and feathers are in particular suitable for this application. The advantage of the spray application is that pollution of the wastewaters is avoided on account of the recovery of the solvent.

In the method of the present invention, the compounds of the formula (1) can also be used in combination with other protectants which act against insects that feed on keratin, for example with urea derivatives, benzimidazoles, aromatic sulfonamides and phosphoric and phosphonic esters.

The amount of active substance of the formula (1) employed depends on the respective substrate and the method of application. However, it is normally such that, after application to the material to be protected, the latter contains about 100 to 200 ppm, preferably 200 to 1000 ppm, of active substance. This corresponds, for example, to concentrations of 0.005 to 1 g/l of treatment bath, depending on the degree of exhaustion, in the exhaust method at a liquor ratio of 1:20. In the pad method, concentrations of up to 2 g/l are possible.

The active compounds of the formula (1) employed in the method of the invention can be obtained by known methods. Reference is made in this connection to German Offenlegungsschrift Nos. 2,335,347 and 2,365,555. The starting materials required for the manufacture of the active compounds are also described in these specifications as well as in German Offenlegungsschrift Nos. 2,231,312, 2,432,951, 2,230,862 and 2,630,633.

The compounds of the formula (1) can be used in the method of the invention both as pure optical isomers and as isomer mixtures such as racemates or mixtures of diastereoisomers. If pure optically active compounds are used as starting materials in the manufacture of the compounds of the formula (1), pure optical isomers can be obtained. If the starting materials are isomer mixtures, then isomer mixtures are usually obtained again. If desired, these isomer mixtures can be separated by conventional methods into diastereoisomers, which in turn can be resolved into the optical antipodes. The compounds eligible for use in the present invention and encompassed by the formula (1) and all other formulae and designations, are to be understood as comprising both the individual isomers and their mixtures.

MANUFACTURING EXAMPLE FOR THE ACTIVE COMPOUNDS 8.01 g (0.04 mole) of m-phenoxybenzyl alcohol and 7.09 g (0.03 mole) of ethyl α-isopropyl-3-methoxyphenylacetate are dissolved in 100 ml of anhydrous toluene and 0.1 g of sodium hydride is added as catalyst. After mounting a 50 cm distillation column, the mixture is heated and stirred. The ethanol which has formed, together with toluene, is distilled off as an azeotropic mixture. The reaction is complete after about 3 hours. The reaction mixture is cooled, then poured into cold water and the layers are separated. The toluene solution is concentrated under reduced pressure, affording as residue 11.5 g of ester, which is purified by chromatography on 55 g of activated alumina with a mixture of benzene/hexane (1:3) as eluant. Yield: 10.12 g (86.4% of theory) of the ester of the formula

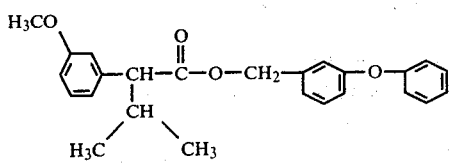
The esters of the formula
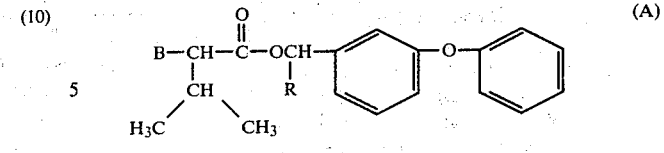
are obtained in similar manner or by one of the other methods described in German Offenlegungsschrift Nos. 2,365,555 or 2,335,347.
Table
| Formula | B | R | $n_D$ |
|---|---|---|---|
| 11 | H₃CO—⌬—, OCH₃ | H | $n_D^{25} = 1.5655$ |
| 12 | H₅C₂O—⌬— | CN | $n_D^{25} = 1.5208$ |
| 13 | H₃CO—⌬— | H | $n_D^{19} = 1.5878$ |
| 14 | H₃CO—⌬— | H | $n_D^{17} = 1.5377$ |
| 15 | H₃CO—⌬—, Cl | H | $n_D^{20} = 1.5467$ |
| 16 | H₃CO—⌬—, Cl | H | $n_D^{20} = 1.5476$ |
| 17 | H₃C—⌬— | H | $n_D^{28,5} = 1.5596$ |
| 18 | Cl—⌬— | —C≡CH | $n_D^{23} = 1.5699$ |
| 19 | H₃C—⌬— | —C≡CH | $n_D^{24} = 1.5611$ |
| 20 | Cl, Cl—⌬— | —C≡CH | $n_D^{22} = 1.5433$ |
| 21 | Br—⌬— | —C≡CH | $n_D^{23} = 1.5329$ |

Table-continued
| | | | |
|---|---|---|---|
| 22 | 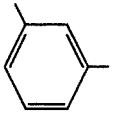 3-F-C₆H₄- | —C≡CH | $n_D^{25} = 1.5625$ |
| 23 | 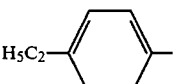 4-H₅C₂-C₆H₄- | —C≡CH | $n_D^{23,5} = 1.5723$ |
| 24 | 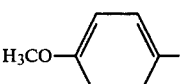 4-H₃CO-C₆H₄- | —C≡CH | $n_D^{22,4} = 1.5622$ |
| 25 | 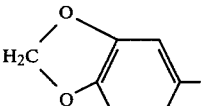 3,4-methylenedioxyphenyl | —C≡CH | $n_D^{24} = 1.5749$ |
| 26 | 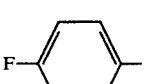 4-F-C₆H₄- | CN | $n_D^{20} = 1.5233$ |
| 27 | 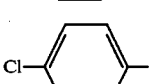 4-Cl-C₆H₄- | H | $n_D^{21} = 1.5655$ |
| 28 | 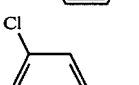 3-Cl-C₆H₄- | H | $n_D^{17} = 1.5722$ |
| 29 | 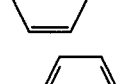 4-F-C₆H₄- | H | $n_D^{23} = 1.5544$ |
| 30 | 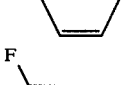 3-F-C₆H₄- | H | $n_D^{21,5} = 1.5543$ |
| 31 | 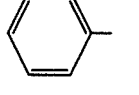 4-Br-C₆H₄- | H | $n_D^{17,5} = 1.5802$ |
| 32 | 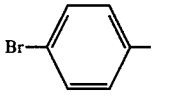 4-H₅C₂-C₆H₄- | H | $n_D^{21,5} = 1.5590$ |
| 33 | 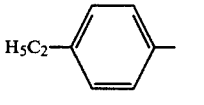 4-(n)H₇C₃-C₆H₄- | H | $n_D^{18} = 1.5542$ |
| 34 | 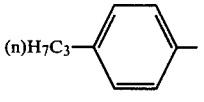 4-(i)H₇C₃-C₆H₄- | H | $n_D^{19} = 1.5548$ |
| 35 | 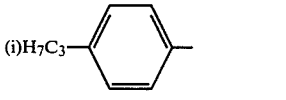 4-(CH₃)₂CH-CH₂-C₆H₄- | H | $n_D^{20} = 1.5327$ |
| 36 | 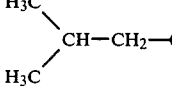 4-CH₃-C₆H₄- | CN | $n_D^{20} = 1.5624$ |

Table-continued

| # | Ar | R | $n_D$ |
|---|----|----|----|
| 37 | Cl—C6H4— | CN | $n_D^{20}= 1.5533$ |
| 38 | H5C2—C6H4— | CN | $n_D^{20}= 1.5239$ |
| 39 | (i)H7C3—C6H4— | CN | $n_D^{20}= 1.5226$ |
| 40 | (CH3)3C—C6H4— | CN | $n_D^{20}= 1.5451$ |
| 41 | C6H5— | H | $n_D^{20}= 1.5638$ |
| 42 | C6H5— | CN | $n_D^{20}= 1.555$ |
| 43 | C6H5— | —C≡CH | $n_D^{20}= 1.5595$ |
| 44 | Cl—C6H4— | —CH=CH2 | $n_D^{35}= 1.5650$ |

The following Examples illustrate the method of the present invention in more detail, but imply no restriction to what is described therein. Parts and percentages are by weight.

EXAMPLE 1 (EXHAUST METHOD)

A 0.4% stock solution of each of the compounds of the formulae (10) to (44) in glycol mono-methyl ether is prepared. Then an aqueous treatment bath containing, in 120 ml of distilled water, 0.12 ml of a wetting agent and dispersant, 0.6 ml of formic acid 1:10 and 0.75 ml of the respective 0.4% stock solution, is prepared at room temperature. Then 3 g of wool flannel are wetted with hot water and put into the bath at room temperature. While constantly circulating the wool sample, the bath temperature is raised to 60° C. in the course of 20 minutes and treatment is carried out for 30 minutes at 60° C. The bath is then cooled, the wool sample rinsed twice for 3 minutes with distilled water, squeezed out by hand and dried in the air. The active substance concentration is 1000 ppm, based on the weight of the wool.

The dried sample is subjected to the mothproofing test (protection against feeding damage caused by the webbing clothes moth *Tineola biselliella* Hum.), in accordance with SNV 195901, and to the resistance test against larvae of the fur beetle (*Attagenus piceus* Ol.) and carpet beetle (*Anthrenus vorax* Wat. ) in accordance with SNV 195902. In these tests, larvae of *Anthrenus vorax* and 6- to 7-week-old larvae of *Attagenus piceus* are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms.

The tested compounds of the formulae (10) to (44) exhibit very good action against the three pests.

EXAMPLE 2 (PAD METHOD)

A 0.4 % stock solution of each of the compounds of the formulae (10) to (44) in glycol mono-methyl ether is prepared. Each of the stock solutions (12.5 ml) is diluted to 50 ml (solution 1) with glycol monomethyl ether which contains 0.65 g/l of a wetting agent and dispersant. Solution 1 (25 ml) is diluted to 50 ml (solution 2) with glycol monomethyl ether which contains 0.5 g/l of a wetting agent and dispersant. Solution 2 (25 ml) is diluted in turn to 50 ml (solution 3) with glycol monomethyl ether which contains 0.5 g/l of a wetting agent and dispersant.

3 ml of each of solutions 1, 2 and 3 are poured into crystallisation dishes and a disc of wool flannel is wetted for 3 seconds therein. The moist discs are then padded between aluminium sheets to a pick-up of 50% of each solution. The concentrations of active substance are, respectively, 500 ppm, 250 ppm and 125 ppm for the discs treated with solutions 1, 2 and 3. The discs are then dried in the air and subjected to the same biological tests as in Example 1. The tested compounds of the formulae (10) to (44) exhibit very good action against all 3 pests, even at the lowest concentration of 125 ppm.

EXAMPLE 3

A 10% solution of α-cyano-3-phenoxybenzyl-α'-isopropyl-4'-methylphenylacetate (compound 36) in glycol monomethyl ether is prepared. One part by volume of this solution is diluted with 200 parts by volume of a solvent suitable for dry cleaning, for example a suitable petroleum fraction or perchloroethylene. If desired, other cleaning promoters can be added. Woollen articles are then treated in the conventional manner in this cleaning fluid and subsequently centrifuged to a solvent pick-up of about 100% of the weight of the wool. After drying, the articles have a moth- and beetle-resistant finish.

A moth- and beetle-resistant fabric is also obtained by substituting a compound of the formulae (10) to (35) or (37) to (44) for α-cyano-3-phenoxybenzyl-α'-isopropyl-4'-methylphenylacetate and repeating the above procedure.

Similar mixtures can also be used for spraying or sprinkling wool in any state of processing.

EXAMPLE 4

A 0.5% solution of the active substance of the formula (36) in methylene chloride, trichloroethylene or a low boiling petroleum fraction is prepared. A woollen article is sprayed with this solution from a conventional spray device, so that 2×15 g/m² of active substance solution is applied, corresponding to a concentration of about 400 ppm on the material at a 30% consumption of the aerosol. The treated woollen fabric has a moth- and beetle-resistant finish.

A moth- and beetle-resistant finish is also obtained by substituting an active substance of the formulae (10) to (35) or (37) to (44) for that of the formula (36) and repeating the above procedure.

What is claimed is:

1. A method of protecting keratinous material from attack by insects that feed on keratin and from feeding damage, which comprises treating the material to be protected with compounds of the formula

[structure]

wherein each of $R_1$ and $R_2$ independently represents hydrogen, fluorine, chlorine, bromine, alkyl of 1 to 4 carbon atoms or alkoxy of 1 to 4 carbon atoms, or $R_1$ and $R_2$ in the ortho-position to each other together represent the methylenedioxy radical, and $R_3$ represents hydrogen, cyano, —C≡CH or —C=CH$_2$.

2. A method according to claim 1, which comprises treating the material to be protected with compounds of the formula

[structure]

wherein each of $R'_1$ and $R'_2$ independently represents chlorine, bromine, methyl or methoxy, or $R'_1$ and $R'_2$ in the 3,4-position together represent the methylenedioxy radical, and $R'_3$ represents hydrogen, cyano or —C≡CH.

3. A method according to claim 1, which comprises treating the material to be protected with compounds of the formula

[structure]

wherein $R''_1$ represents hydrogen, fluorine, chlorine, bromine, alkyl of 1 to 4 carbon atoms or alkoxy of 1 to 4 carbon atoms and $R'_3$ represents hydrogen, cyano or —C≡CH.

4. A method according to claim 3, which comprises treating the material to be protected with compounds of the formula

[structure]

wherein $R'''_3$ represents fluorine, chlorine, bromine, methyl or methoxy and $R'''_3$ represents cyano or —C≡CH.

5. A method according to claim 3, which comprises treating the material to be protected with a compound of the formula

[structure]

$R'''_3$ represents hydrogen or —C≡CH.

6. A method according to claim 2, which comprises treating the material to be protected with a compound of the formula

[structure]

wherein $R''_3$ represents cyano or —C≡CH.

7. A method according to claim 4, which comprises treating the material to be protected with a compound of the formula

[structure]

wherein $R'_1{}^v$ represents chlorine or methyl and $R''_3$ represents cyano or —C≡CH.

8. A method according to claim 1, wherein the active substances are applied to the material to be protected in an amount of 100 to 2000 ppm, preferably 200 to 1000 ppm, based on the weight of said material.

9. A method according to claim 1 for protecting raw or processed wool, wool blends, hides and furs.

10. A method according to claim 9 for providing a wash- and lightfast finish against attack by moths and beetles.

11. A method according to claim 1, which comprises treating wool fabrics by the exhaust method in an aqueous liquor which contains the active substance and, if desired, one or more dispersants or other assistants customarily employed in dyeing.

12. A method according to claim 1, which comprises treating wool fabrics by the pad method with an aqueous liquor which contains the active substance and, if desired, one or more dispersants or other assistants customarily employed in padding.

13. A method according to claim 1, which comprises treating the material to be protected with an organic cleaning fluid which contains one or more of the compounds defined in claim 1.

14. A method according to claim 1, which comprises spraying onto the material to be protected an organic solvent which contains one or more of the compounds defined in claim 1.

15. The keratinous material protected according to claim 1.

16. Keratinous material according to claim 15, preferably woollen goods, furs and hides containing 100 to 2000 ppm, preferably 200 to 1000 ppm, of one or more of the compounds defined in claim 1.

17. A composition for protecting woollen goods, furs and hides, which contains one or more of the compounds defined in claim 1.

* * * * *